United States Patent [19]
Yamada et al.

[11] Patent Number: 6,017,765
[45] Date of Patent: Jan. 25, 2000

[54] FLUORESCENCE DETECTION CAPILLARY ARRAY ELECTROPHORESIS ANALYZER

[75] Inventors: Takashi Yamada, Tokyo; Hideki Kambara, Hachioji, both of Japan

[73] Assignee: Hitachi, Ltd., Tokyo, Japan

[21] Appl. No.: 09/026,720

[22] Filed: Feb. 20, 1998

[30] Foreign Application Priority Data

Feb. 24, 1997 [JP] Japan .................................. 9-039463

[51] Int. Cl.[7] .................................................. G01N 27/26
[52] U.S. Cl. ........................... 436/47; 422/64; 422/82.08; 204/602; 204/604
[58] Field of Search ................................... 422/63, 64, 65, 422/67, 82.08; 436/43, 47, 161, 172; 204/600–605

[56] References Cited

U.S. PATENT DOCUMENTS

| | | |
|---|---|---|
| 5,045,172 | 9/1991 | Guzman . |
| 5,062,942 | 11/1991 | Kambara et al. . |
| 5,162,654 | 11/1992 | Kostichka et al. . |
| 5,356,525 | 10/1994 | Goodale et al. . |
| 5,384,024 | 1/1995 | Moring et al. . |
| 5,413,686 | 5/1995 | Klein et al. . |
| 5,424,037 | 6/1995 | Zimmermann et al. . |
| 5,529,679 | 6/1996 | Takahashi et al. . |
| 5,772,966 | 6/1998 | Maracas et al. . |
| 5,922,617 | 7/1999 | Wang et al. . |

OTHER PUBLICATIONS

Analytical Chemistry, vol. 67, No. 13, Jul. 1, 1995, "High–Speed DNA Sequencing by Using Mixed Poly(ethylene oxide) Solutions in Uncoated Capillary Columns", E. Fung et al, pp. 1913–1919.

Analytical Chemistry, vol. 64, No. 8, Apr. 15, 1992, "Capillary Array Electrophoresis Using Laser–Excited Confocal Fluorescence Detection", X. Huang et al, pp. 967–972.

Analytical Chemistry, vol. 66, No. 9, May 1, 1994, "Simultaneous Monitoring of DNA Fragments Separated by Electrophoresis in a Multiplexed Array of 100 Capillaries", K. Ueno et al, pp. 1424–1431.

*Primary Examiner*—Jeffrey Snay
*Attorney, Agent, or Firm*—Beall Law Offices

[57] ABSTRACT

A fluorescence detection capillary array electrophoresis analyzer comprising a capillary array holder holding a plurality of capillary array units and a transferring unit for transferring in turn the capillary array units held by the capillary array holder to a sample injection station, a fluorescence detection station or a gel refresh station, which reduces the time required for pre-electrophoresis and replacement of a used gel by fresh gel, and conducts efficient and automatic analysis. Furthermore, the analyzer automatically discharges residual samples remaining in the capillaries, and hence automatically analyzes a large number of samples by electrophoresis.

22 Claims, 11 Drawing Sheets

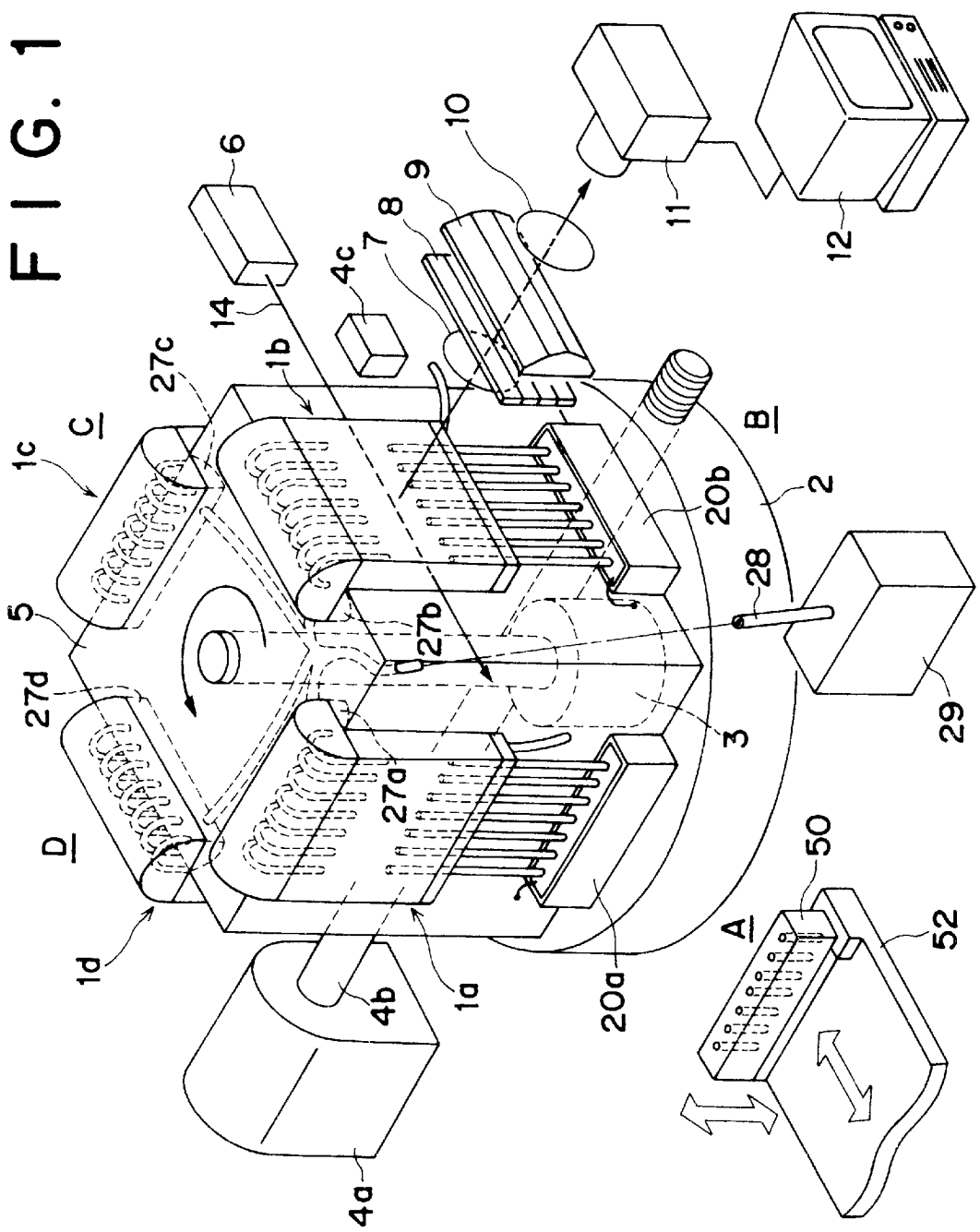

F I G. 5A
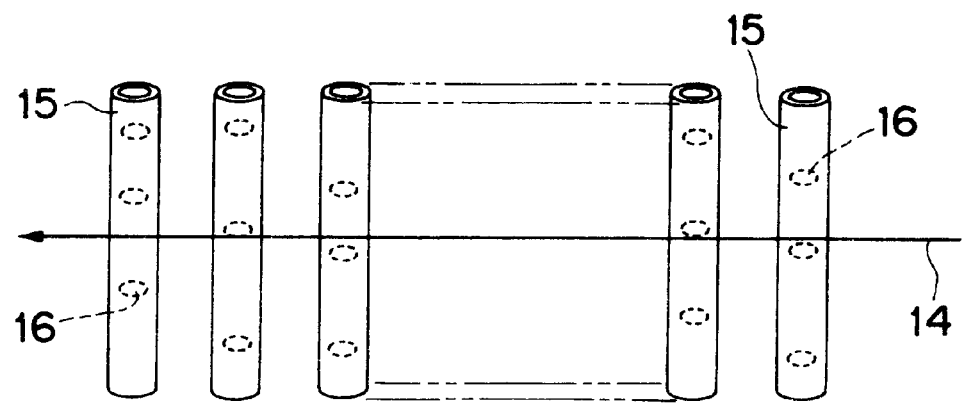
F I G. 5B
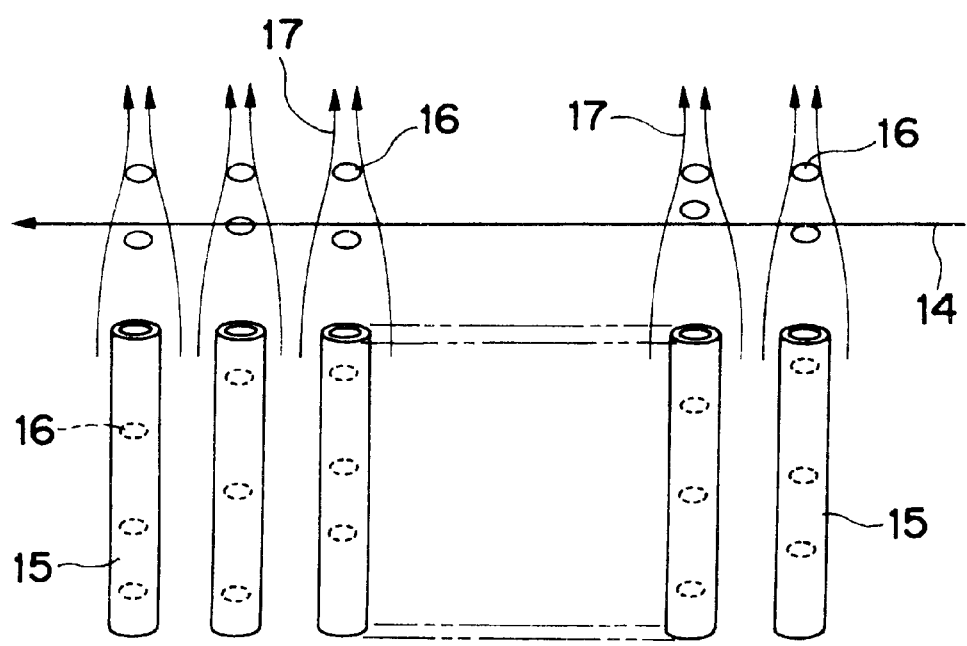

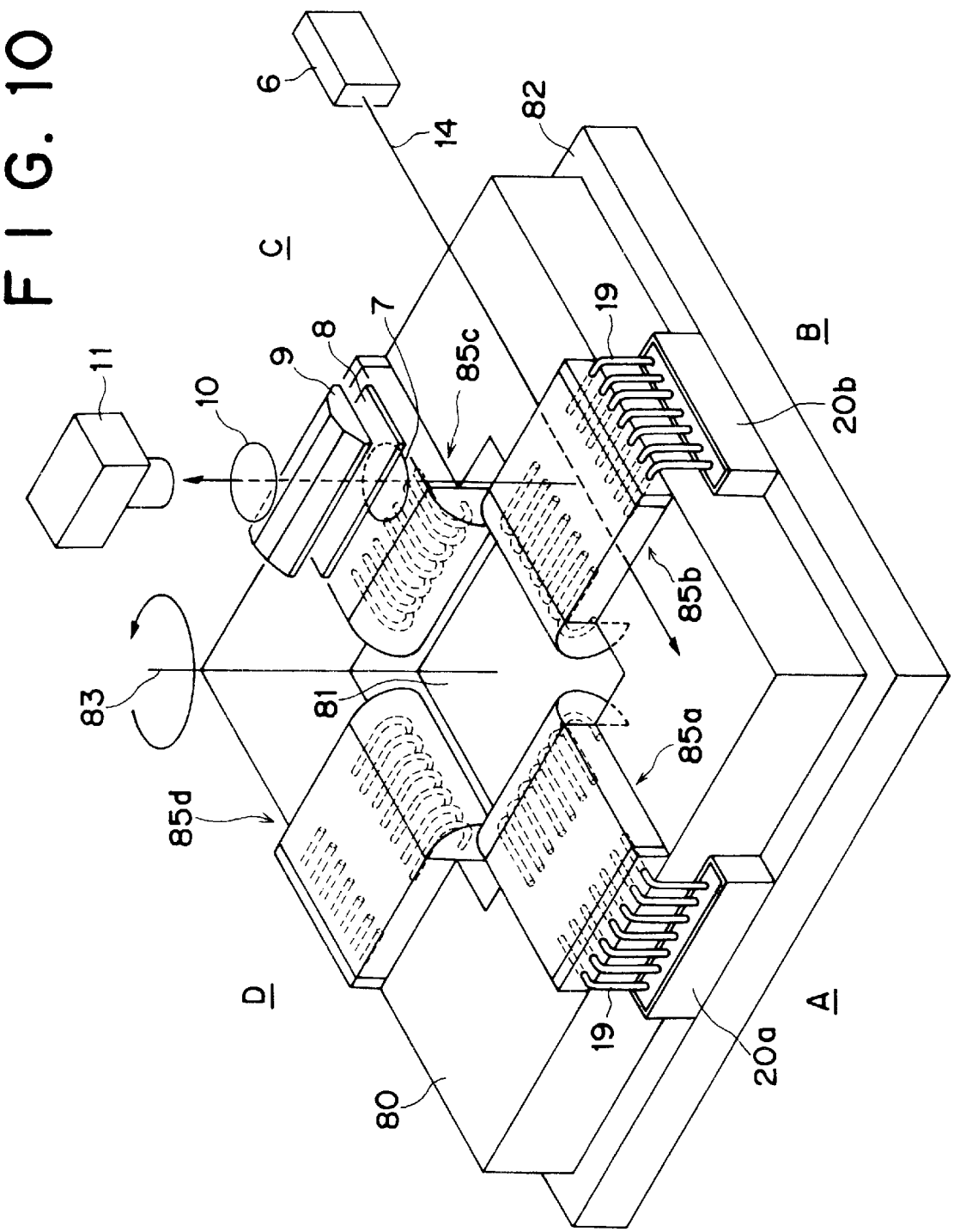

FLUORESCENCE DETECTION CAPILLARY ARRAY ELECTROPHORESIS ANALYZER

BACKGROUND OF THE INVENTION

1. Field of the Invention

This invention relates to a fully automated gel electrophoresis system using fluorescence detection capillary array electrophoresis for analyzing a large number of biological samples such as DNAS, RNAs, peptides, and proteins.

2. Description of the Related Art

With the advance of genome project, there is a growing demand for a high-speed and high-throughput DANA analysis system. Fluorescent DNA sequencers employing gel electrophoresis for separating DNA fragments have been used for DNA sequencing as well as DNA fragment analysis. These conventional systems use a slab gel plate made of polyacrylamide gel sandwiched between two plates. As to the shape of the gel, there are slab gels and gels packed in capillary tubes. In conventional systems, troublesome gel exchange should be manually carried out for each measurement. Therefore, there has been a desire for the development of a fully automated system in which gel exchange is fully automatically carried out. A promising method for full automation and rapid and high-throughput analysis is a capillary gel electrophoresis using a narrow capillary packed with a separation medium. The use of capillary array gel electrophoresis permits high-throughput and rapid DNA analysis because this electrophoresis can use a large number of electrophoresis lanes capable of analyzing many samples and can be rapidly carried out by applying a high electric field without a large amount of Joule's heat. The separation part in this electrophoresis system is composed of a capillary array and it is much easier to handle than slab gel plates because the capillary array is lighter than the slab gel.

On the other hand, there has been reported a method using a polymer gel as a separation medium in place of a crosslinked polyacrylamide. In systems using capillary tubes, there is a growing tendency that the same capillary tubes are repeatedly used after evacuating the used polymer gel and packed with fresh polymer gel. In these systems, after the completion of a measurement, the used polymer gel is pushed out of the capillary tubes to be replaced by fresh polymer gel and the next measurement is automatically carried out.

In electrophoresis separation and measurement, pre-electrophoresis or pre-running is carried out at first by applying an electric current to a gel without injecting DNA samples. The pre-electrophoresis is a cleaning-up process of the gel or a separation medium to remove impurities disturbing fluorescence measurements. Then, samples such as fluorophore-labeled DNA fragments are electrically injected into the separation medium. After the injection, electrophoresis is carried out at a constant voltage to separate the DNA fragments according to their length, and the DNA fragments are optically detected by fluorescences emitted from the DNA fragments at a detection portion several tens centimeters apart from the injection portion.

Examples of fluorescence detection electrophoresis analyzers of prior art have been disclosed in U.S. Pat. No. 5,529,679, U.S. Pat. No. 5,062,942 and U.S. Pat. No. 5,162,654.

SUMMARY OF THE INVENTION

A large-scale DNA analysis, as well as a large-scale analysis of biological samples, such as genome analysis, analysis for DNA diagnostics, and soon, requires a high-throughput operation of an analysis system where a lot of samples have to be efficiently and automatically analyzed in a short period of time. The use of a polymer gel as a separation medium is good for full automation but does not always give a sufficient resolution. When the polymer gel is used, the same capillaries can be used only less than 100 times. It is still necessary to replace the capillary tubes every 100 times of measurements. In addition, it takes a lot of time to replace the used gel polymer with fresh one, carry out pre-electrophoresis and inject samples into capillaries. Therefore, there is desired the advent of a more easily usable and fully automated system which permits high-throughput and rapid analysis.

An object of the present invention is to provide an electrophoretic analysis system which uses an electrophoresis medium such as a polymer gel or a polyacrylamide gel, reduces the time required for pre-electrophoresis and replacement by fresh polymer gel, conducts efficient and automatic analysis, and realizes efficient and fully automatic analysis of biological samples.

The system according to the present invention has a plurality of capillary array units (a conventional electrophoresis system usually has one separating unit).In this system, a sample injection step, an analysis step by electrophoresis, and a gel replacing or residual-DNA-fragments removing step are carried out at different positions (stations).

In the present invention, the capillary array units are injected in turn with fluorophore-labeled samples, and transferred one after another to a fluorescence detection station where an electrophoretic pattern is detected.

Before the detection, injection of samples into the capillary array unit and pre-electrophoresis are carried out in a sample injection station. The capillary array units containing samples which are not or being electrophoresed are transferred in turn to the fluorescence detection station. In the fluorescence detection station, the samples are irradiated with laser beams while migrating further, and fluorescences emitted by the fluorophore labels are measured to detect DNA fragments or the like, whereby a real-time electrophoretic pattern is detected for a definite time.

The above procedure is explained below by taking the case of one of the capillary array units. The capillary array unit stops at the first station where fluorophore-labeled samples are injected into the gel-packed capillaries of the unit and migrate until just before a time when the shortest fragments of the samples reach the detecting region. Then, the capillary array unit moves to the second station where fluorescences emitted from migrating DNA bands are detected for a predetermined period of time. Subsequently, the capillary array unit moves to the third station where the used gel is replaced by fresh gel and pre-electrophoresis is carried out. As to the fluores-cence detection at the second station, each capillary array unit ready for the fluorescence measurement comes to the second station where the fluorescence measurement is carried out efficiently without loss time. Each capillary array unit stays in the fluorescence detection station only for a period required for detecting fluorescences emitted from the DNA fragments passing through the detecting portion.

After completion of the fluorescence measurement, the capillary array unit is replaced by another capillary array unit which is transferred to the fluorescence detecting station. Consequently, DNA analysis is carried out continuously and efficiently in a minimum analysis time. The capillary array unit after completion of the detection of the electrophoretic pattern is then transferred to the third station (gel refresh station) where the separation medium (gel) is replaced by fresh one or the residual DNA fragments in the capillary array are removed by additional electrophoresis. Thus, the capillary array units are subjected successively to the sample injection and pre-electrophoresis, the electrophoresis and real-time electrophoresis pattern detection using fluorescence, and the sample removal by the additional electrophoresis, which are carried out in parallel with one another. Therefore, when the system is used, the analysis can be carried out in the shortest time.

The fluorescence detection capillary array electrophoretic analysis system of the present invention is characterized by being equipped with a capillary array holder holding a plurality of capillary array units, and a transferring unit for transferring the capillary array units held by the capillary array holder to the sample injection station, the fluorescence detection station or the gel refresh station, respectively, at the same time.

The capillary array holder has a plurality of capillary array units mounted on a turn table and moves among stations (i.e. the sample injection station, the fluorescence detection station and the gel refresh station(s)) located around it at a certain angle with one another. The capillary array units stop in turn at the stations, respectively, by the rotation of the capillary array holder.

Alternatively, the capillary array holder may have a plurality of capillary array units mounted on a sliding plate and moves among stations (i.e. the sample injection station, the fluorescence detection station and the gel refresh station (s)) located on a plane, and the transferring unit may slide the capillary array holder on a sliding plate along the above-mentioned plane.

Each capillary array unit is transferred to the sample injection station, the fluorescence detection station and then the gel refresh station(s). In the fluorescence detection station, fluorescences emitted from migrating DNA fragments or other biological samples are detected in real time. In the gel refresh station, cleaning-up of the capillaries or refreshing of the separation medium is carried out by replacing the separation medium by fresh one or removing the residual DNA fragments by electrophoresis.

The capillary array unit is equipped with a capillary array packed with a electrophoresis medium such as a gel or a polymer, and a fluorescence detecting cell inside which sheath-flows are formed and fluorescences emitted from separated DNA fragments or biological compounds are detected in the sheath-flows. In this case, the cell is filled with a buffer solution and the ends of the capillaries are placed in the cell so that the separated DNA fragments may be eluted from the capillary ends to be irradiated with laser beams for the fluorescence detection.

Alternatively, the capillary array unit is equipped with a capillary array packed with an electrophoresis medium such as a gel or a polymer, and optical windows on capillary columns, respectively, for fluorescence detection in which each capillary of the capillary array unit is irradiated with laser beams and fluorescences emitted from DNA fragments migrating in the separation medium inside the capillary columns are detected.

As the separation medium, a crosslinked ges as acrylamide or various kinds of polymer gels are used (Anal. Chem. 67, 1913–1919 (1995)).

The capillaries in the capillary array are arrayed in a plane near or in a laser beams irradiation region, and a laser beam irradiates samples migrating in a sheath-flow formed outside the end of each capillary or on samples migrating in each capillary.

Fluorophore-labeled DNA fragments or other biological samples are irradiated with laser beams to emit fluorescences after or during being separated by electrophoresis in the capillaries filled with separation medium. The fluorescences are detected with a photodetector such as an array sensor. A photomultiplier detector, line sensor, area sensor, or two-dimensional camera system can be used as the detector.

Of course, there are several alternative methods for irradiating biological samples separated in capillaries filled with separation medium. One of them is laser scanning on capillaries (Anal. Chem. 64, 967–972 (1992)). In this method, the capillaries are irradiated one by one to detect migrating DNA fragments or other biological samples. Another is as follows: the capillaries in the capillary array are arrayed in a plane near or in a laser beams irradiation region and irradiated in turn with scanned laser beams from the outside of the above-mentioned plane, whereby samples migrating in each capillary (or samples migrating in as sheath-flow formed outside the end of each capillary)are irradiated with the laser beams. Still another is as follows: the capillaries are irradiated at the same time with laser beams expanded into a line by a beam expander, whereby samples migrating in the capillaries(or samples migrating in a sheath-flow formed outside the end of the capillary) are irradiated with the laser beams (Anal. Chem. 66, 1424–1431 (1994)).

Fluorescences emitted from fluorophore labels irradiated by the laser beams are detected with a one-dimensional or two-dimensional photodetector. As the photodetector, a line sensor, an area sensor or an optoelectronic amplifier is used. To distinguish fluorescences emitted by different color (fluorophore)tags or labels, a color (wavelength) selective detection is carried out. The fluorescences can be subjected to wavelength separation (color separation) by means of a wavelength-dispersing element (e.g. a diffraction grating or a prism) or a combination of an image-splitting means (e.g. a polyhedral prism or a splitting lens) and band pass filters. A moving wheel with color(wavelength) filters may also be used for color (wave-length) selective fluorescence detection. An image splitting method coupled with color (wavelength) filters may also be used. Although the image splitting method is adopted in the examples given herein, other methods may, of course, be adopted as well.

According to the present invention, DNAs or the like can be fully automatically analyzed by electrophoresis by providing an automatic sample injection device and an device for automatic transfer of electrophoresis units. By using a polymer or a repeatedly usable crosslinked polyacrylamide gel as an electrophoresis medium, DNA sequencing or fragment analysis can be efficiently repeated merely by feeding measurement samples. In this case, the residual DNA samples in the capillaries can be removed from the capillaries by additional electrophoresis and pre-electrophoresis which are carried out after the measurement. Since the sample injection is carried out before transferring the capillary array unit to the fluorescence detection station, each capillary array unit stays in the light irradiation region for a period sufficiently long for the measurement. Therefore, the measurement can be efficiently repeated in a cycle time which is far shorter than the turn around time required for the conventional capillary array system having one capillary array unit.

The present invention is very advantageous in reducing the analysis time by separating the real-time fluorescence detection step from the steps of preparing conditions necessary for the repeated analysis operations with the capillary array system. Actually, the employment of a replaceable gel in the capillary array system permits fully automated and repeated operations. However, it takes a lot of time for the separation medium (gel) replacement, pre-electrophoresis, sample injection, and electrophoresis until signal appearance. The present invention solves the problem of time-consuming steps other than the real-time fluorescence detection step by using a plurality of capillary array units and carrying out various procedures necessary for the fluorescence detection outside the fluorescence detection station. The total analysis time is a period required for the analysis not including the other procedures, and the system permits efficient and repeated analysis operations. For example, in the case of a rapid analysis, the analysis time is as short as 10 minutes, except that the time required for small DNA fragments to migrate to the detection region is 5 minutes. However, the sample injection requires 10 minutes, the separation medium replacement 15 minutes, and the pre-electrophoresis 15 minutes. The present inventive system using five or six capillary array units can reduce the total analysis time to 13–15 minutes. When a capillary array unit composed of 100 capillaries can be rapidly operated for 24 hours, almost 2,400 samples can be analyzed. Therefore, the system of the present invention can analyze about 10,000 samples, namely, it permits far more efficient analysis.

The present invention is summarized below with reference to FIG. 1. In the electrophoretic analysis system of the present invention, a plurality of capillary array units 1a to 1d are fixed in a capillary array holder 5, which is mounted on a turn table and rotated stepwise to move the capillary array units in turn to a sample injection station A, a fluorescence detection station B or a gel refresh station C or D. In the sample injection station A, sample injection into the capillary array and pre-electrophoresis are carried out. In the fluorescence detection station B, fluorescence is detected while electrophoresing samples. In the gel refresh station C or D, the residual samples in the capillary array are removed by additional electrophoresis. The present invention permits reduction of the time required for pre-electrophoresis and replacement by fresh gel, and efficient and automatic measurement. Furthermore, the present invention permits automatic electrophoresis analysis of a large number of samples by repeated measurements by automatic discharge of the residual samples remaining in the capillaries.

BRIEF DESCRIPTION OF THE DRAWINGS

FIG. 1 is a schematic illustration showing an example of electrophoretic analysis system according to the present invention.

FIG. 2A is a perspective view of the whole unit, and FIG. 2B is a schematic cross-sectional view of the unit.

FIG. 4A is a diagram showing the relationship among the positions of the sample injection instrument, a capillary array and electrodes, and FIG. 4B is a schematic view showing a condition in which samples are injected.

FIGS. 5A and 5B show the relationship between the positions of the capillary array according to the present invention and laser beams and illustrate methods for irradiating migrating DNA fragments with the laser beams.

FIG. 10 is a schematic illustration showing another example of electrophoretic analysis system according to the present invention.

DESCRIPTION OF THE PREFERRED EMBODIMENTS

Figure 2A:
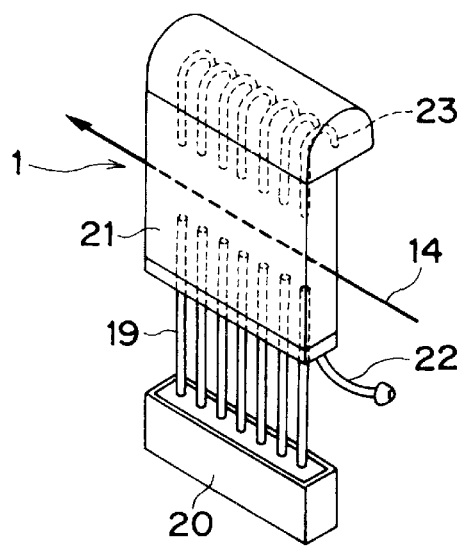
FIGS. 2A and 2B are schematic diagrams showing an example of capillary array unit according to the present invention.

The embodiments of the present invention are explained below with reference to the drawings.

FIG. 1 is a schematic illustration showing an example of electrophoretic analysis system according to the present invention. This electrophoretic analysis system is equipped with a capillary array holder 5 which support capillary array units 1a, 1b, 1c and 1d on its four sides, respectively. The capillary array holder 5 is on a turn table 2 so that it can be rotated. A sample injection station A, a fluorescence detection station B and gel refresh stations C and D are located around the capillary array holder 5. The motor 3 rotates the capillary array holder 5 by steps of 90° to move the capillary array units 1a, 1b, 1c and 1d to the sample injection station A, the fluorescence detection station B, the gel refresh station C and then the gel refresh station D.

In the sample injection station A, sample injection into the capillary array unit 1a by means of a sample injection instrument 50 and subsequent pre-electrophoresis are carried out. In the fluorescence detection station B, laser beam 14 irradiates the capillary array unit 1b from aside while electrophoresing samples, and fluorescence emitted from the samples are wavelength selectively detected through a filter 8 and a prism 9 with a camera 11. In the gel refresh stations C and D, additional electrophoresis is carried out by further applying a voltage to the capillary array unit 1c or the capillary array Unit 1d, which has been subjected to fluorescence detection, whereby residual samples in the capillaries are removed.

A lead screw 4b rotatable by a motor 4a is screwed into the stage 2. When the motor 4a is worked, the lead screw 4b is rotated, whereby the stage 2 is moved in the direction of axis of the lead screw 4b together with the capillary array holder 5 mounted thereon. By pressing the fluorescence detection station B side of the capillary array holder 5 on a guide member 4c, the capillary array unit 1b at the fluorescence detection station B is positioned in relation to the optical axis of laser beam 14.

Figure 2B:
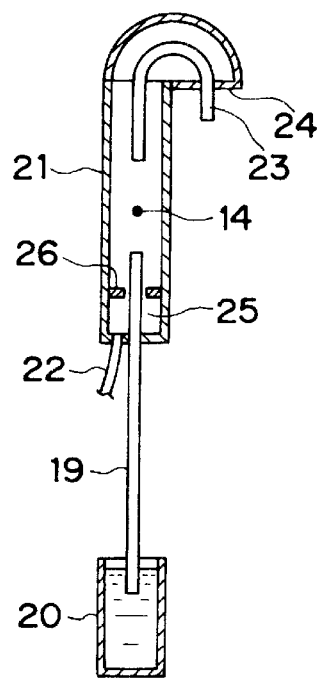

FIGS. 2A and 2B are schematic diagrams showing an example of capillary array unit: FIG. 2A is a perspective view of the whole unit, and FIG. 2B is a schematic cross-sectional view of the unit. The capillary array unit 1 is composed of a capillary array 19, a buffer solution vessel 20, a fluorescence detecting cell (sheath-flow cell) 21, a buffer solution inlet tube for sheath-flow 22 and drains 23. The capillary array 19 is, for example, an array of a plurality of capillaries obtained by packing a polyacrylamide gel or a polymer gel into quartz tubes with an inside diameter of 0.075 mm and an outside diameter of 0.2 mm.

The outlet end of the capillary array 19 and the inlet end of the drain 23 face each other at a definite distance. As shown in FIG. 2B (the cross-sectional view), the outlet end of the drain 23 is projected from an upper wall surface 24 tightly closing the fluorescence detecting cell 21. A fluorescence detection region through which laser beams 14 pass is located between the outlet end of the capillary array 19 and the drains 23 in the fluorescence detecting cell 21. In the fluorescence detection region, samples migrating in each sheath-flow pass through the irradiated region to emit fluorescence.

In the lower part of the fluorescence detecting cell 21, there is provided a room containing buffer solution 25 which has an upper partition plate 26 and is supplied with a buffer solution through the buffer solution inlet tube for sheath-flow 22. The partition plate 26 has holes with a diameter somewhat larger than the outside diameter of the capillary, in the same number as the number of capillaries of the capillary array 19, and the capillaries of the capillary array 19 extend to the inside of the fluorescence detecting cell 21 through the holes of the partition plate 26. The lower end of the capillary array 19 is immersed in the buffer solution in the buffer solution vessel 20.

In the upper part of the capillary array holder 5, pools 27a to 27d of buffer solution for sheath-flow are provided. The capillary array units 1a to 1d are fixed on the capillary array holder 5 so that the outlet ends of the drains 23 of the capillary array units 1a to 1d may be located in the pools 27a to 27d, respectively. Each of the pools 27a to 27d is tightly closed with the upper wall surface 24 (see FIG. 2B). A tube 28 extending from each of the pools 27a to 27d is connected to a draining vessel 29 located below buffer solution vessels 20a to 20d.

The flow of the buffer solution for sheath-flow in the capillary array unit is explained below with reference to FIG. 1, FIG. 2A and FIG. 2B. The buffer solution for sheath-flow supplied to the capillary array unit 1 from a buffer solution supply vessel for sheath-flow (not shown) through the buffer solution inlet tube for sheath-flow 22 flows upward through the capillaries of the capillary array unit 1 owing to the gravity difference, enters one of the pools 27a to 27d of the capillary array holder 5, and then is discharged into the draining vessel 29 through the tube 28. In the capillary array unit 1, the buffer solution for sheath-flow enters the room containing buffer solution 25, at first, passes around each capillary in the hole portion of the partition plate 26 having the capillary penetrating therethrough, flows so as to encircle each capillary, and enters the fluorescence detecting cell 21. Then, the buffer solution for sheath-flow enters the drain 23 and flows into one of the pools 27a to 27d of the capillary array holder 5 through the outlet end of the drain 23.

Electrodes are immersed in the buffer solutions in the buffer solution vessels 20a to 20d and the pools 27a to 27d, and a voltage is applied between the electrode (a common electrode) immersed in the buffer solution in each of the pools 27a to 27d and the electrodes immersed in the buffer solution in each of the buffer solution vessels 20a to 20d. The voltage applied may be different in the different stations, i.e., the sample injection station A, the fluorescence detection station B and the gel refresh stations C and D.

Next, a measuring method using the electrophoretic analysis system shown in FIG. 1 is explained below. The four capillary array units 1a to 1d can beset on the capillary array holder 5 shown in FIG. 1. Before measurement, the four capillary array units 1a to 1d are set on the capillary array holder 5. Samples such as DNA fragments are injected into the capillary array 19 from the end of the capillary array 19 on the buffer solution vessel 20 side in the sample injection station A. At the beginning of measurement, the buffer solution vessel 20 of the capillary array unit 1a at the sample injection station A is replaced by the sample injection instrument 50. The replacement is automatically carried out with a robot arm 52 or the like.

Figure 3:
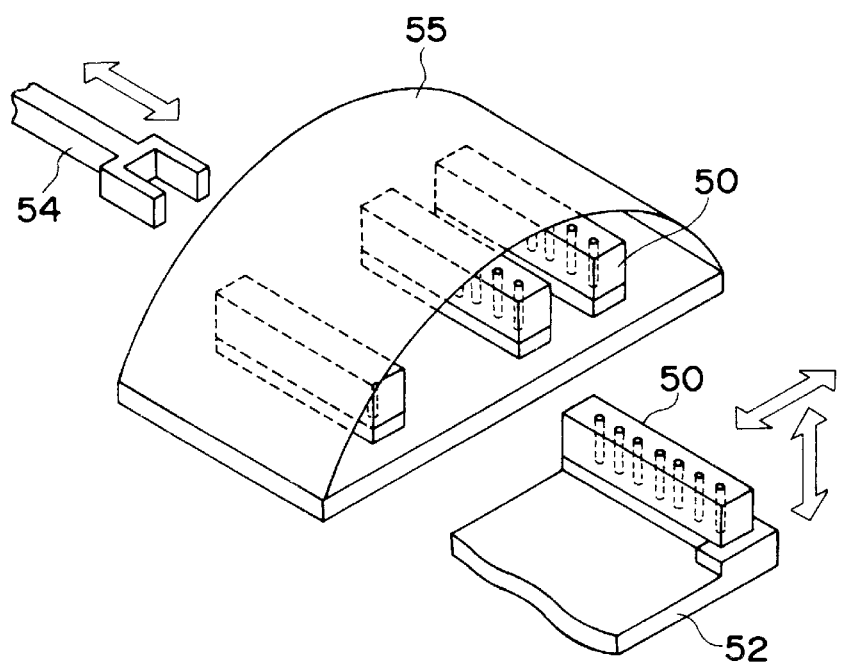
FIG. 3 is a schematic view showing a method for transferring a sample injection instrument according to the present invention.

FIG. 3 is a schematic view showing a method for transferring the sample injection instrument. The sample injection instruments 50 are stored in a low-temperature and high-humidity atmosphere in a sample storage booth 55. An arm 54 takes out the sample injection instrument 50 containing samples to be analyzed next, from the sample storage booth 55, and places the instrument 50 on the arm 52. The arm 52 loaded with the sample injection instrument 50 moves in the directions of arrows shown in FIG. 3 to convey the sample injection instrument 50 to a position near the sample injection station A. Subsequently, the buffer solution vessel 20a on the stage 2 is held by a robot arm (not shown) and transferred to a temporary storage place, and the sample injection instrument 50 on the arm 52 is attached to the lower part of the capillary array unit 1a.

Figure 4A:
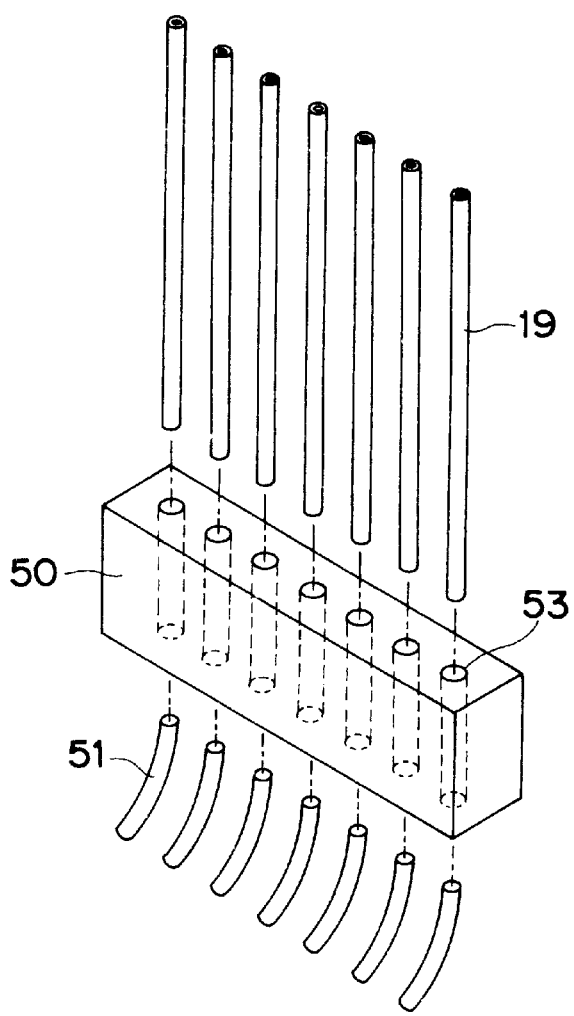
FIGS. 4A and 4B show the details of the sample injection instrument according to the present invention.
Figure 4B:
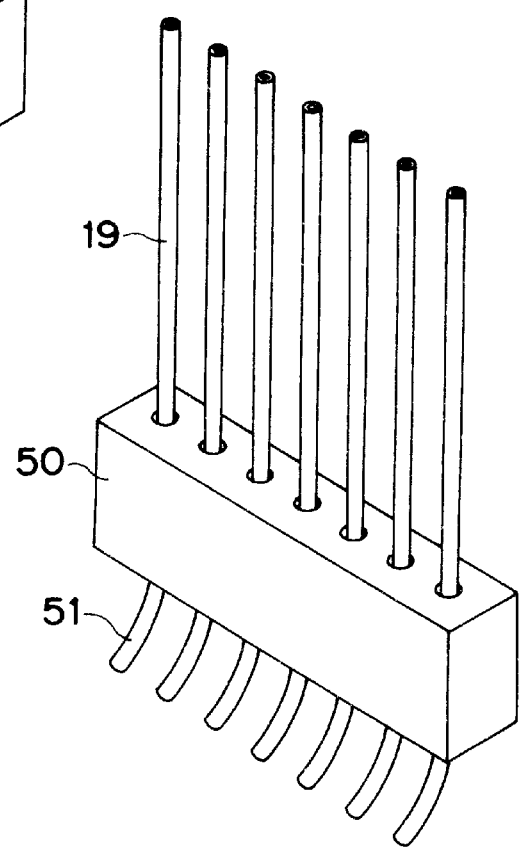

FIGS. 4A and 4B show the details of the sample injection instrument: FIG. 4A is a diagram showing the relationship among the positions of the sample injection instrument, the capillary array and the electrodes, and FIG. 4B is a schematic view showing a condition in which the samples are injected. The sample injection instrument 50 is a block made of acrylic resin, polypropylene, glass or the like and having through-holes 53 with a diameter of about 1 mm in the same number as the number of capillaries of the capillary array 19. DNA fragments are held in each through-hole 53 owing to the capillarity. After the buffer solution vessel 20a is replaced by the sample injection instrument 50, the lower end of capillary of the capillary array 19 and the electrode 51 are inserted into each through-hole 53 of the sample injection instrument 50 containing the DNA fragments, from both sides, respectively, of the sample injection instrument 50 as shown in FIG. 4B, and a voltage is applied between the electrode 51 and an electrode connected to the pool 27a, whereby the DNA fragments are injected into capillary array 19 by applying an electric field. In the insertion of the lower end of the capillary array 19 and the electrodes 51 into the sample injection instrument 50, the end of the capillary is put in each through-hole 53 of the sample injection instrument 50 by moving the sample injection instrument 50 with a robot arm while keeping the original position of the end of the capillary. Then, the electrode is inserted into each through-hole 53 of the sample injection instrument 50 with a robot arm. The voltage applied during the injection by the electric field application is approximately 0.1–1.5 kV and is chosen depending on the concentrations of the DNA fragments and the length of migration in the capillary.

After completion of the injection of the DNA fragments in the sample injection station A, the sample injection instrument 50 is replaced by the buffer solution vessel 20a with the robot arm 52 or the like, and a voltage is applied between the electrodes immersed in the buffer solution in the buffer solution vessel 20a and the electrode immersed in the buffer solution in the pool 27a to carry out electrophoresis for a predetermined time until short DNA fragments such as primers reach positions just before the outlet ends of the capillaries. The voltage applied in this case is 100 V/cm. Although the predetermined electrophoresis time is about L minutes when the length of migration in the capillary is taken as L cm, it depends on the concentration of the polyacrylamide. After the predetermined time (L minutes), the motor 3 is worked to rotate the capillary array holder 5, whereby the capillary array unit 1a containing the samples is positioned at the fluorescence detection station. After the rotation by the motor 3, the fluorescence detection station B side of the capillary array holder 5 is pressed on the guide member 4c. By this positioning by the use of the guide member 4c, the laser beams irradiation region of the capillary array unit 1b placed at a predetermined position in the fluorescence detection station B is accurately irradiated with laser beams 14.

In the capillary array unit 1b placed at the predetermined position in the fluorescence detection station B, DNA fragments have migrated to positions near the outlet of each capillary of the capillary array 19, i.e., positions just before a sheath-flow, and fluores-cences emitted from the DNA fragments are immediately begun to be measured by continuing the electrophoresis at 100 V/cm. In the next capillary array unit set at the sample injection station A in place of the capillary array unit 1a, its buffer solution vessel 20 is automatically replaced by a sample injection device 50 in the same manner as above, whereby DNA fragments are injected into the capillary array 19 of the set capillary array unit. Thus, short DNA fragments among the DNA fragments injected into each capillary from the sample injection station A migrate to positions just before a sheath-flow in about 60 minutes in which the detection is completed in the fluorescence detection station B. Therefore, the detection can be continued without waiting time by transferring the capillary array unit at the sample injection station to the fluorescence detection station B.

The DNA fragments injected into the capillary array 19 migrate to the fluorescence detecting cell 21 side in the fluorescence detection station B and are irradiated with laser beams 14 in the fluorescence detecting cell to emit fluorescences. In the fluorescence detecting cell 21, sheath-flows are formed of a buffer solution supplied through the buffer solution inlet for sheath-flow 22. The electrophoresed DNA fragments are eluted into the sheath-flow flowing upward, and irradiated with the laser beam 14. The buffer solution forming the sheath-flow in the fluorescence detecting cell 21 is discharged through the drains 23.

FIGS. 5A and 5B show the relationship between the positions of the capillary array and laser beam and illustrate the method of irradiating DNA fragments migrating in the flow. As the methods of laser irradiation, there are two cases as shown in FIGS. 5A and 5B. The case 5A is the on-column detection where DNA fragments 16 migrating in capillaries 15 are irradiated with laser beams 14 from the outside of the capillaries 15. The case 5B is the sheath-flow method, where DNA fragments 16 eluted into a sheath-flow 17 from capillaries 15 are irradiated with laser beam 14.

Figure 6A:
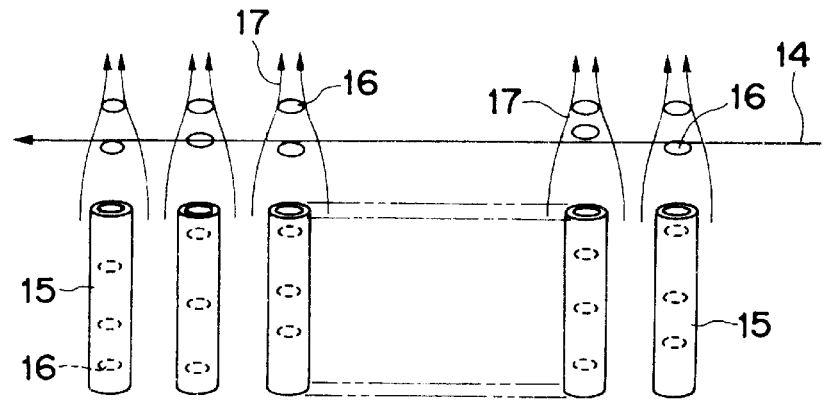
FIGS. 6A, 6B and 6C illustrate methods for irradiation with laser beams according to the present invention.
Figure 6B:
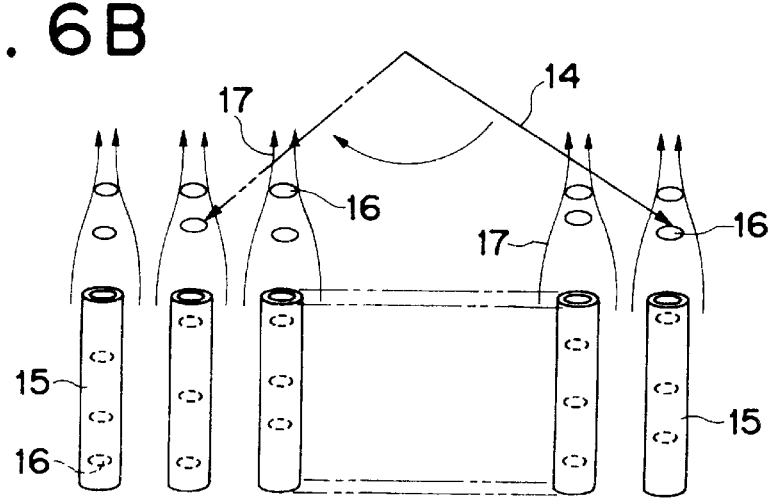
Figure 6C:
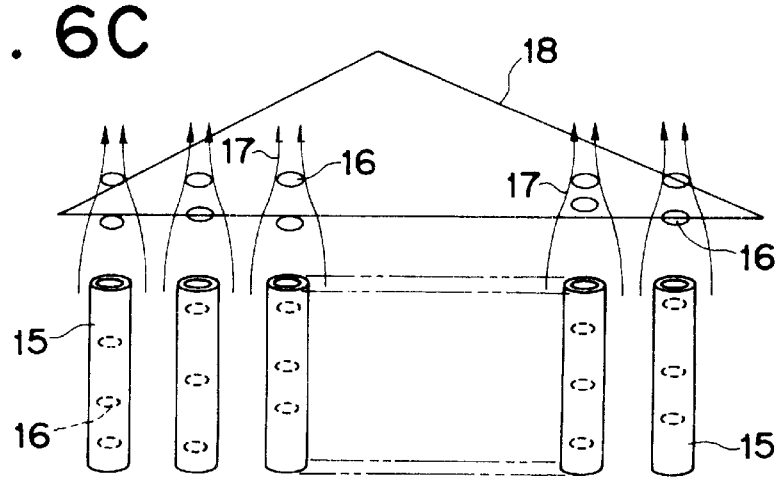

In addition, there are three laser irradiation techniques shown in FIGS. 6A, 6B and 6C, respectively. FIG. 6A shows side entry laser irradiation technique in which laser beam 14 is introduced from the side of a plane formed by capillaries 15 arrayed in a plane, to irradiate all the electrophoresis lanes simultaneously. FIG. 6B shows a laser scanning technique in which electrophoresis lanes corresponding to capillaries 15, respectively, are irradiated in turn by scanning the laser beam 14. FIG. 6C shows a technique in which laser beams are expanded to irradiate all the electrophoresis lanes from a direction perpendicular to a plane formed by capillaries 15 arrayed in a plane.

In the electrophoretic analysis system shown in FIG. 1, there are employed the method shown in FIG. 5B, i.e., the method using the sheath-flows 17, and the introduction-from-aside technique shown in FIG. 6A. In said system, there may be employed any combination of either of the two methods shown in FIGS. 5A and 5B and one of the three techniques shown in FIGS. 6A, 6B and 6C. When the introduction-from-aside method is adopted, laser beams 14 should be passed through a space of 0.1 to 0.2 mm between two glass plates constituting the fluorescence detecting cell 21, so that the positioning accuracy of the laser beam in the cell on the capillary array holder 5 should be about 20 μm or less. The precision of position of the capillary array holder 5 is assured by pressing the side of the capillary array holder 5 on the guide member 4c by working the motor 4a. When the precision of machinery is sufficient, the positioning using the guide member 4c is not necessary.

DNA fragments are labeled with four kinds of fluorophores having different emission wavelengths for their respective terminal base species. Therefore, the terminal base species can be distinguished by measuring the wavelengths of fluorescences emitted by the fluoro-phores. The base sequence of the DNA can be determined by knowing the time of the fluorescence detection and the terminal base species. The four fluorescence emission wavelengths are detected in distinction from one another as follows in the electrophoretic analysis system shown in FIG. 1: fluorescence emitted from the DNA fragments is collected by a lens 7, separated according to wavelength by four kinds of band pass filters 8 and an image splitting prism 9, passed through a lens and detected with a CCD camera 11, a two-dimensional area sensor while spatially separated according to wavelength. The detection results obtained by means of the CCD camera 11 are input to a computer 12 to be processed.

Figure 7:
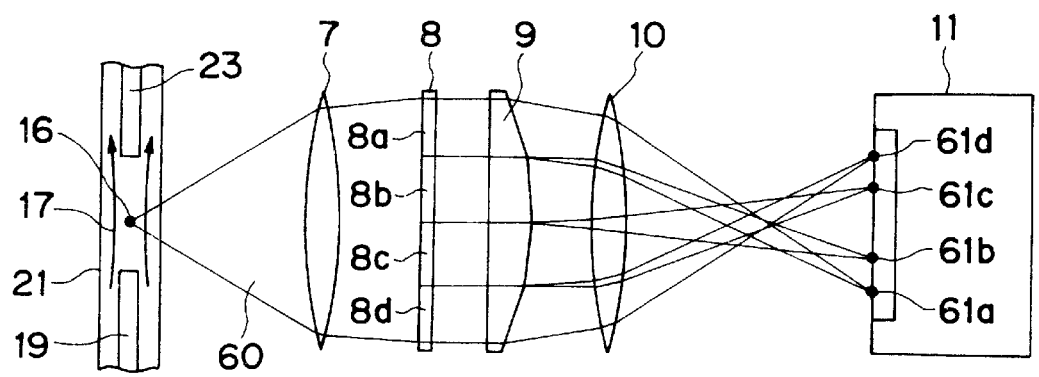
FIG. 7 illustrates an example of wavelength separation of fluorescences according to the present invention.

FIG. 7 illustrates the wavelength separation (color separation) of fluorescence by the use of the band pass filters 8 and the image splitting prism 9. Each DNA fragment 16 is eluted from the capillary array 19 and passes through path of the laser beam which is perpendicular to the page of FIG. 8. Fluorescence 60 is emitted from a fluorophore label irradiated with the laser beam during migration. The fluorescence 60 is color-selectively detected with a CCD camera after passing through the image splitting prism equipped with the four kinds of the filters 8a, 8b, 8c and 8d, respectively, which selectively transmit fluorescences, respectively, and it is focused with a focusing lens 10 to form images apart from one another on different lines 61a to 61d, respectively, in the CCD camera 11.

For example, when the wavelength of the fluorescence emitted from the DNA fragment 16 is such that the fluorescence is transmitted by the band pass filter 8a, a fluorescence image of the DNA fragment 16 is projected on the line 61a and nothing appears on the other lines 61b, 61c and 61d. Similarly, when the wavelength is such that the fluorescence is transmitted by the band pass filter 8b, a fluorescence image of the DNA fragment 16 is projected only on the line 61b in the CCD camera 11. Thus, the kind of the fluorophore, i.e., the terminal base species can be determined from the light reception position on light reception surface of the CCD camera 11.

Figure 8:
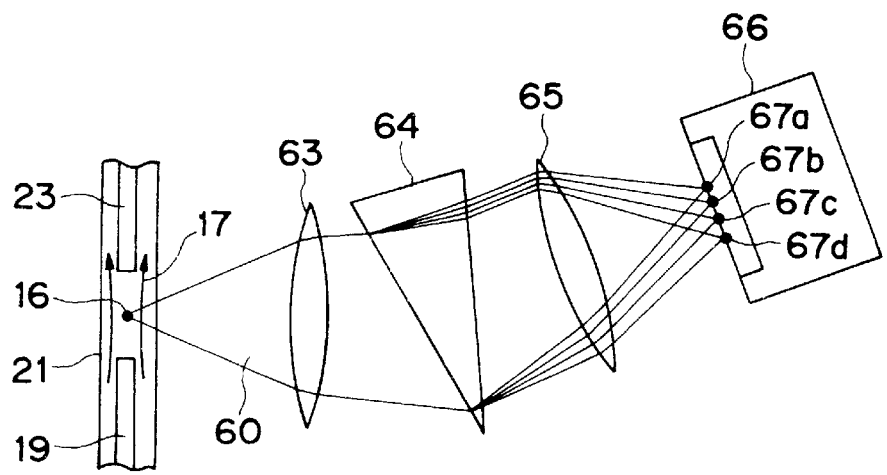
FIG. 8 illustrates another example of wavelength separation of fluorescences according to the present invention.

FIG. 8 illustrates another example of wave-length selective detection methods. In the case shown in FIG. 8, the wavelength separation of fluorescence is carried out using a wavelength dispersion element such as a prism or a diffraction grating. Each DNA fragment 16 is eluted from the capillary array 19 and passes through the laser irradiated region which is perpendicular to the page of FIG. 8, in the course of migration to the drain 23 in the sheath-flow 17, whereby fluorescence 60 is emitted by a fluorophore label irradiated with the laser beams. The fluorescence 60 is collected by a lens 63 and subjected to wavelength dispersion by a wavelength dispersion element 64 such as a prism. The fluorescences subjected to wavelength dispersion form images apart from one another on different lines 67a to 67d, respectively, for different wavelengths on the light reception surface of a detector 66, owing to an imaging lens 65. The detector 66 may be either an area sensor or a line sensor.

The wavelength separation of fluorescence can be carried out by still another method employing a photomultiplier tube, laser scanning and a rotary filter. In this case, a fluorescence detecting cell, the rotary filter equipped with 4 band pass filters set in the circumferential direction, and the photomultiplier tube are located in a straight line in that order. Fluorescences emitted from the fluorescence detecting cell pass through the rotary filter and are detected with the photomultiplier tube.

An electric field is further applied on each of the capillary array units 1c and 1d in the gel refresh stations C and D, respectively, moved from the fluorescence detection station B. This electric field application is for removing residual DNA fragments which have not yet reached the light irradiation region in the fluorescence detection station B, from the capillary array. When the electric field applied to each of the capillary arrays at the gel refresh stations C and D, respectively, is 200 V/cm, the DNA fragments are removed in about 60 minutes. Therefore, although the capillary array holder 5 shown in FIG. 1 is equipped with the four capillary array units 1a to 1d, continuous operation is possible without any trouble even when the number of capillary array units set on the capillary array holder 5 is 3 in all. When the number of capillary array units set is 3, the capillary array holder 5 is a triangular block.

The capillary array units can be reused after the gel is refreshed. In detail, when once set on the capillary array holder 5, each of the four capillary array units 1a to 1d moves in turn to the fluorescence detection station B in about 60 minutes in which the detection of 500 bases of each DNA specimen is completed. The detection is automatically carried out until the analysis of all specimens previously set is completed. The analysis in each electrophoresis unit is usually completed in about 1 hour and makes it possible to determine the sequence of 500 bases. Each capillary array can be used 3 or 4 times. Therefore, when each capillary array unit has 96 capillaries, 1,100 to 1,500 (96×4×3 to 96×4×4) specimens can be analyzed a day, and this number corresponds to 550 k to 750 k bases/day and is a throughput more than ten times as high as that of a conventional analyzer.

All of the adjustment of temperature and humidity of the sample storage booth, the control of the robot arms for sample injection, the control of the motor 3 for rotating the capillary array holder 5, the control of the motor 4a for translating the capillary array holder 5, the on-off control of a voltage applied to each capillary array unit, the control of the laser 6, the control of initiation and termination of sample analysis, the analysis of measurement data, etc. are systematically carried out by control circuits, whereby the electrophoretic analysis system is automatically operated. When the capillary array holder 5 has a pentagular or higher-order polygonal shape such as a hexagonal shape or an octagonal shape, the number of settable capillary array units can be increased to 6, 8 or the like. In this case, when capillary array units are once set on the capillary array holder of the electrophoretic analysis system, the system is automatically operated for 24 hours and the base sequence determination of 2,300 specimens (1150 k bases) can be carried out a day.

Although in the case shown in FIG. 1, the sample injection is carried out in the lower part of the capillary array holder 5 and DNA fragments injected into the lower ends of the capillaries are electrophoresed upward, DNA fragments may be electrophoresed downward by turning the capillary array 19 and the direction of sheath-flow upside down.

Figure 9A:
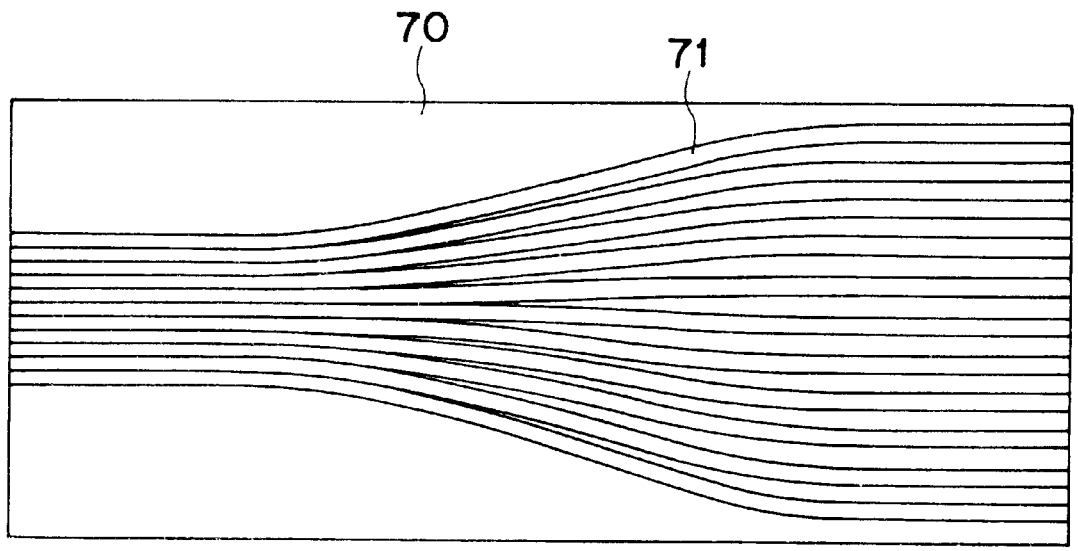
FIG. 9A is an illustration of a capillary array forming device according to the present invention.
Figure 9B:
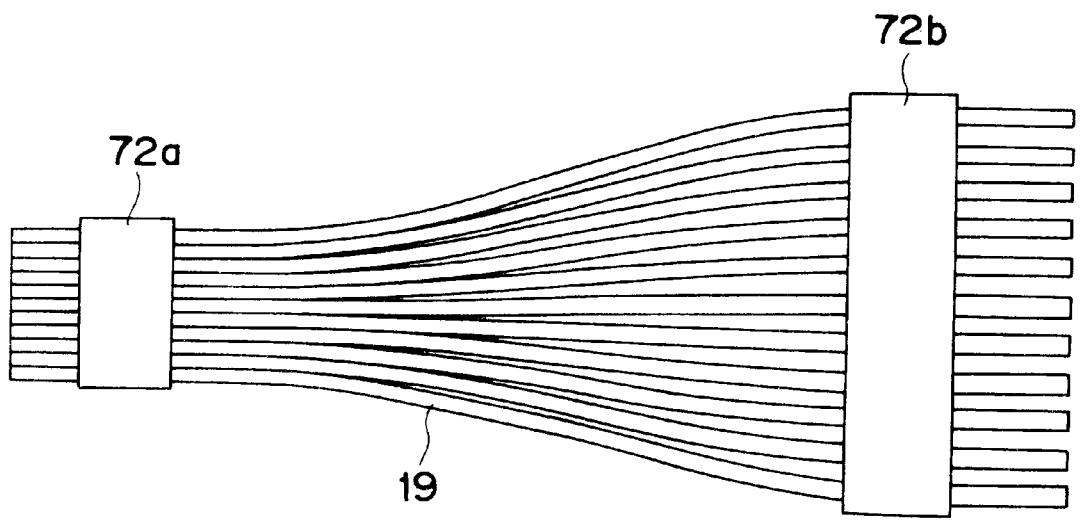
FIG. 9B is an illustration of a formed capillary array according to the present invention.

FIG. 9A is an illustration of an example of capillary array forming device. The capillary array 19 of each of the capillary array units 1a to 1d is formed as shown in FIG. 9B, by putting capillaries in each groove 71 of a capillary guide 70 and fixing both ends or the whole of the resulting capillary array with tapes 72a and 72b or a resin, respectively. By such a forming process, a large number of capillary arrays can easily be produced.

FIG. 10 is a schematic illustration showing another example of electrophoretic analysis system of the present invention. In the system explained in FIG. 1, the capillary array units 1a to 1d are set on the capillary array holder 5, though in the electrophoretic analysis system explained in FIG. 10, capillary array units are set on the top surface of a capillary array holder. This capillary array holder 80 is a square block with a flat top surface having a concave portion 81 in the center. A step portion 82 is formed on the periphery of the capillary array holder 80 and four buffer solution vessels 20a, 20b, - - - are set on the step 82 so as to be located in the center of each side. Four capillary array units 85a to 85d are horizontally fixed on the top surface of capillary array holder 80. The lower ends of gel-packed capillary arrays 19 of the capillary array units 85a to 85d are located in the buffer solution vessels 20a, 20b, - - - . Although each of the capillary array units 85a to 85d has the same structure as that of the electrophoresis unit explained in FIG. 1, FIG. 2A and FIG. 2B, their capillary arrays 19 are curved. Buffer solution supply vessels for supplying a buffer solution for sheath-flow to the capillary array units 85a to 85d, buffer solution draining vessels for accumulating eluted buffer solution, etc. are not shown in FIG. 10.

A sample injection station A, a fluorescence detection station B and gel refresh stations C and D are provided around the capillary array holder 80, and the capillary array units 85a to 85d move in turn to the stations A, B, C and then D by rotating the capillary array holder 80 around a rotation axis 83 by steps of 90°. As in the electrophoretic analysis system explained in FIG. 1, sample injection into the capillary array unit 85a by the use of a sample injection instrument and subsequent pre-electrophoresis are carried out in the sample injection station A. In the fluorescence detection station B, laser beam 14 is arranged in parallel with the top surface of the capillary array holder 80 from the side of the capillary array unit 85b while electrophoresing samples. Fluorescenes emitted from the samples are detected with a camera 11 with wavelength separation using a filter 8 and a prism 9 which are located above the capillary array holder 80. In the gel refresh stations C and D, the residual samples in the capillaries are removed by further applying an electric field to the capillary array units 85c and 85d subjected to fluorescence detection. All of the control of the robot arms for sample injection, the control of rotation of the capillary array holder 80, the on-off control of an electric field applied to each capillary array unit, the control of the laser 6, the control of initiation and termination of sample analysis, the analysis of measurement data, etc. are systematically carried out by control circuits, whereby the electrophoretic analysis system is automatically operated.

Figure 11:
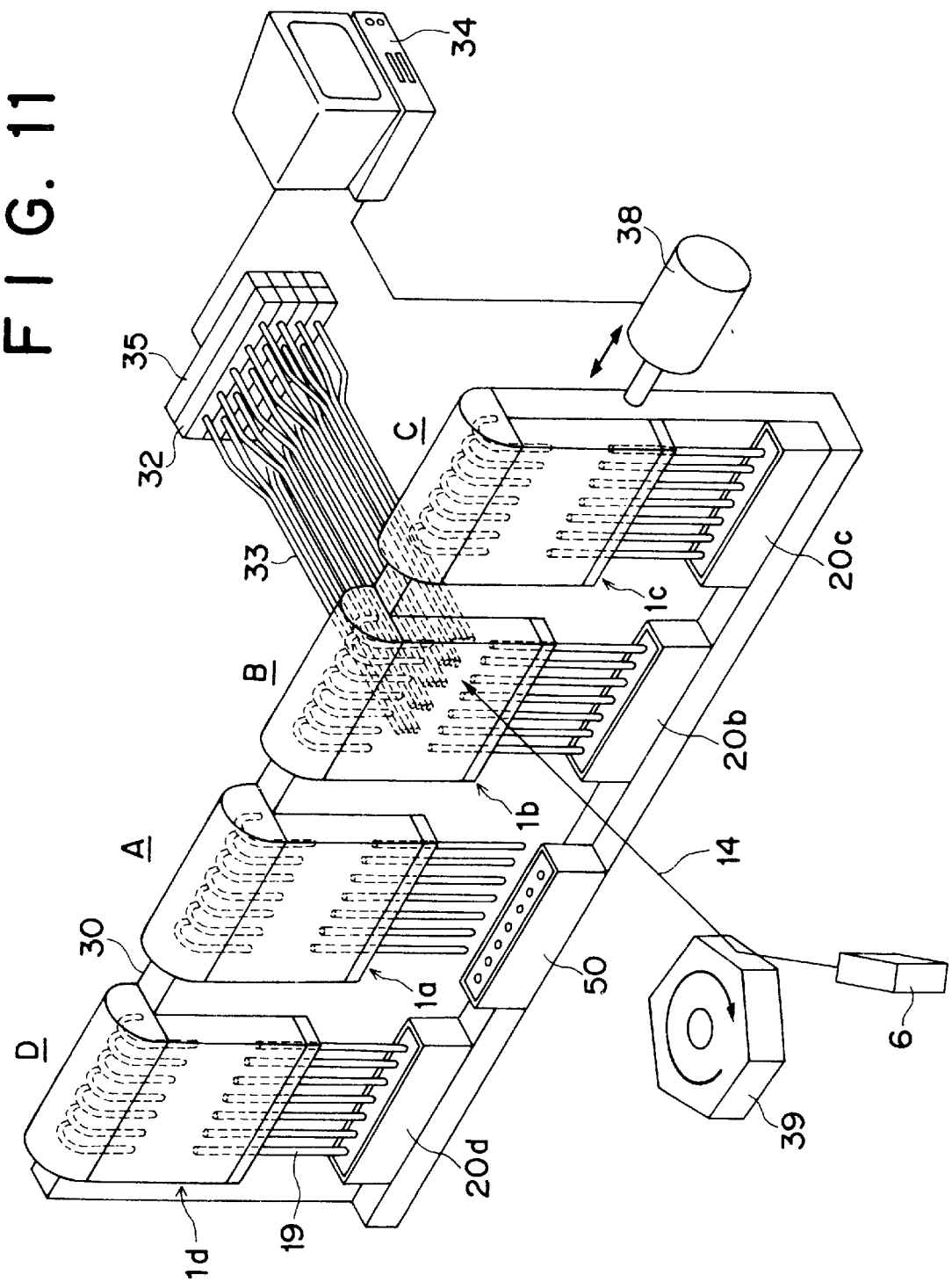
FIG. 11 is a schematic illustration showing further another example of electrophoretic analysis system according to the present invention.
Figure 12:
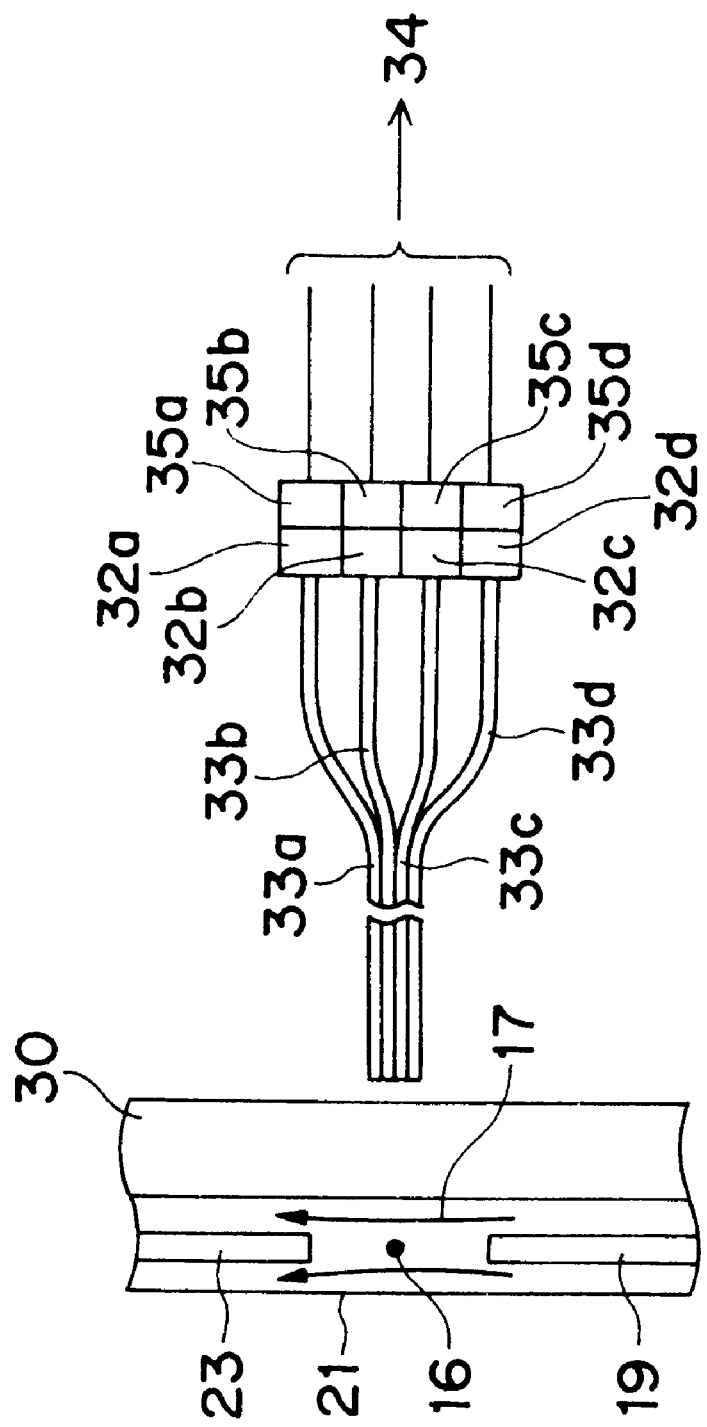
FIG. 12 is a schematic cross-sectional view of a fluorescence detection station according to the present invention.

FIG. 11 is a schematic illustration showing further another example of electrophoretic analysis system of the present invention. FIG. 12 is a schematic cross-sectional view of the fluorescence detection station of the electrophoretic analysis system. In this electrophoretic analysis system, capillary array units 1a to 1d move to a sample injection station A, a fluorescence detection station B, a gel refresh station C and then a gel refresh station D. The capillary array units 1a to 1d are set side by side on a moving substrate 30 which slides horizontally. At least the fluorescence taking-out portion of the moving substrate 30 is transparent. Each of the capillary array units 1a to 1d has the same structure as that of the electrophoresis unit explained in FIG. 2A and FIG. 2B. Each capillary array unit is equipped with a buffer solution inlet tube for supplying a buffer solution for sheath-flow from a buffer solution vessel, and drain tubes for a buffer solution into a draining vessel. The buffer solution inlet tube and the tubes are not shown in FIG. 11. Laser beam 14 irradiates the detection region of the capillary array unit 1b at the fluorescence detection station B from a direction perpendicular to a plane formed by the capillary array, while being scanned.

At the beginning of analysis, the buffer solution vessel of the capillary array unit 1a at the sample injection station A is automatically replaced by a sample injection device 50, and DNA fragments are injected into the capillary array by applying an electric field between capillaries and the samples. The applied voltage for the injection is approximately 0.1–1.5 kV. After completion of the injection of the DNA fragments at the sample injection station shown in FIG. 11, the sample injection device 50 is changed with a buffer solution vessel 20, and an electric field is applied to the capillary array to carry out electrophoresis until short DNA fragments reach the positions just before each sheath-flow. The voltage applied in this case is 100 V/cm and the electrophoresis time is about L minutes when the length of migration in the capillary is taken as L cm in this condition.

Then, the capillary array unit 1a containing the samples moves to the fluorescence detection station B by sliding the transferring substrate 30 with a driving unit 38 such as a motor. In the capillary array unit 1a moved to the fluorescence detection station B, the short DNA fragments such as primers have reached the positions just before each sheath-flow, so that the detection of fluorescence emitted from DNA fragments is immediately started. In a capillary array unit moved to the sample injection station A in place of the capillary array unit 1a, its buffer solution vessel 20 is automatically replaced by a sample injection device 50 in the same manner as above, whereby DNA fragments are injected into the capillary array.

In the fluorescence detection station B, electrophoresis is carried out at 100 V/cm. In this case, at the sample injection station A, short fragments such as primers among the injected DNA fragments migrate to positions just before each sheath-flow in about 60 minutes in which the detection is completed in the fluorescence detection station B. Therefore, fluorescence detection can be immediately carried out by transferring the capillary array unit at the sample injection station A to the fluorescence detection station B, followed by electrophoresis.

A voltage is further applied to each of the capillary array units transferred to the gel refresh stations C and D, respectively, from the fluorescence detection station B. This voltage application is for removing DNA fragments which have not yet reached the light irradiation region at the time of completion of the detection in the fluorescence detection station B, from the capillary array by additional electrophoresis. The capillary array units freed of these DNA fragments can be reused while containing the used gel. In detail, when once set in the system, each of the four capillary array units 1a to 1d is transferred in turn to the fluorescence detection station in about 60 minutes in which the detection of 500 bases of each DNA specimen is completed. The detection is automatically carried out until the analysis of all specimens previously set is completed. Needless to say, a fluid polymer gel may be used as a separation medium while replacing the polymer gel by fresh one.

In the fluorescence detection station B, by scanning laser beams 14 from the laser 6 by reflection from a rotating polygon mirror 39, DNA fragments eluted into a sheath-flow from each capillary in the capillary array 19 are irradiated in turn with the laser beams. Owing to the laser beams irradiation, fluorescences are emitted by fluorophores attached to the DNA fragments. In the vicinity of positions at which a laser beams scanning course and each electrophoresis lane intersect each other, the ends of optical fibers 33 at which fluorescence is introduced are located so that a transparent transferring substrate 30 may be placed between said positions and said ends. The fluorescences emitted by the fluorophores are introduced into filters 32 through the optical fibers 33, and the fluorescences sorted by the filters 32 are detected by line sensors 35, respectively.

As schematically shown in FIG. 12 (the enlarged sectional side view), a set of four optical fibers 33a to 33d is provided for each electrophoresis lane. The end of each of the optical fibers 33a to 33d at which fluorescence is introduced faces to the inter-section of laser beam 14 and the electrophoresis lane, i.e., a position (a fluorescence detection position) at which DNA fragments 16 emit fluorescence. The fluorescence emitted from the DNA fragments 16 are introduced into four band pass filters 32a to 32d with different transmission wavelength bands by the four optical fibers 33a to 33d, respectively. Lights transmitted by the band pass filters 32a to 32d, respectively, are detected by line sensors 35a to 35d, respectively, and analyzed by a computer 34.

Figure 13:
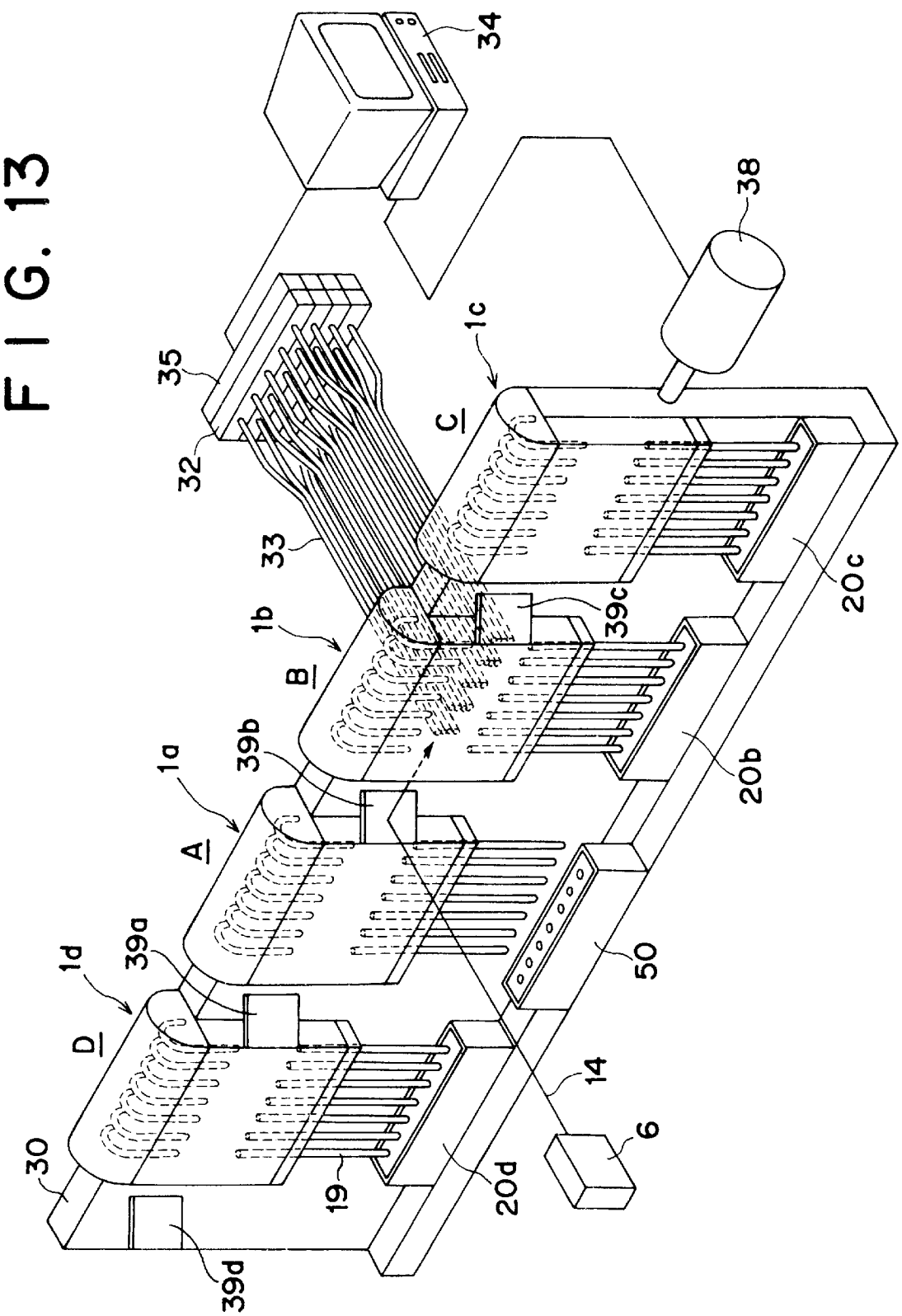
FIG. 13 is a schematic illustration showing still another example of electrophoretic analysis system according to the present invention.

FIG. 13 is a schematic illustration showing still another example of electrophoretic analysis system of the present invention. The system shown in FIG. 13 is different only in laser beams irradiation method from the system shown in FIG. 11. Detailed descriptions of the same parts as in FIG. 11 are omitted by giving the same symbols as in FIG. 11 to these parts. Mirrors 39a to 39d are fixed on a transferring substrate 30 by the side of capillary array units 1a to 1d, respectively. Laser beam 14 hits the mirror 39b fixed beside the capillary array unit 1b placed at a fluorescence detection station B. The laser beam 14 reflected from the mirror 39b is introduced into a fluorescence detecting cell from the side of the capillary array unit 1b to be casted on samples eluted into sheath-flows from the end of the capillary array. Fluorescences emitted from the samples are transmitted by the transferring substrate 30, conducted into filters 32 by optical fibers 33, separated according to wavelength, and then detected by line sensors 35. The detection results are analyzed by a computer 34.

Although the systems using four capillary array units are described in the above embodiments, the present invention is applicable to all electrophoretic analysis systems equipped with two or more capillary array units.

We claim:

1. A fluorescence detection capillary array electrophoresis analyzer comprising:
   a plurality of capillary array units for electrophoresing samples labeled with fluorophores,
   a capillary array holder holding said capillary array units, and
   a transferring unit for transferring said capillary array units in turn to a fluorescence detection station at which migrating samples are irradiated with a laser beam and fluorescence emitted from said fluorophores is detected.

2. An analyzer according to claim 1, wherein there is a sample injection station for injecting fluorophore-labeled samples into each of said capillaries, as a station different from said fluorescence detection station.

3. An analyzer according to claim 1, wherein there is a medium replacing station for replacing the electrophoresis medium of each of said capillaries or a sample removing station for removing the residual samples remaining in each of said capillaries, as a station different from said fluorescence detection station.

4. An analyzer according to claim 1, wherein the transfer or movement of said capillary array units is carried out by rotating a turntable.

5. An analyzer according to claim 1, wherein the transfer of said capillary array units is carried out by sliding a table holding said capillary array units on a plane.

6. An analyzer according to claim 1, wherein there is a sample injection station for injecting fluorophore-labeled samples into each of said capillary array units, and a medium replacing station for replacing the electrophoresis medium of each of said capillary array units with fresh medium or for removing the residual samples remaining in each of said capillary array units, as a plurality of stations different from said fluorescence detection station.

7. An analyzer according to claim 1, wherein each of said capillary array units is equipped with a capillary array packed with an electrophoresis medium, and a fluorescence detecting cell inside which sheath-flows are formed and said fluorescence are detected through the cell.

8. An analyzer according to claim 1, wherein each of said capillary array units is equipped with a capillary array packed with an electrophoresis medium, and an on-column light irradiation fluorescence detection region for detecting said fluorescence emitted from fluorophore labeled samples.

9. An analyzer according to claim 1, wherein the capillaries of said capillary array are arrayed in a plane near or in a region which is irradiated with said laser beam, and said laser beam irradiates said samples from the direction parallel with said plane.

10. An analyzer according to claim 1, wherein the capillaries of said capillary array are arrayed in a plane near or in a region which is irradiated with said laser beam, and said laser beam irradiates said samples from the outside of said plane.

11. An analyzer according to claim 1, wherein all the capillaries of each of said capillary array units are placed in a plane near or in a region which is irradiated with said laser beam, and said laser beam is scanned to irradiate successively said capillaries.

12. An analyzer according to claim 1, which further comprises a one-dimensional or a two-dimensional photodetector for detecting said fluorescence.

13. An analyzer according to claim 1, wherein a photodetector for detecting said fluorescence is located at said fluorescence detection station and moves relatively to the capillaries of each of said capillary array units.

14. An analyzer according to claim 1, wherein a device for separating and detecting the wavelength of said fluorescence is located at said fluorescence detection station.

15. An analyzer according to claim 12, which further comprises a wavelength dispersion element for separating said fluorescence according to wavelength.

16. An analyzer according to claim 12, which further comprises an image-splitting means for splitting fluorescence images formed by said fluorescence, and a band pass filter for separating said fluorescence according to wavelength.

17. A fluorescence detection capillary array electrophoresis analyzer comprising:
   a plurality of capillary array units,
   a capillary array holder holding the plurality of said capillary array units at different stations, respectively, and
   a transferring unit for transferring the plurality of said capillary array units in order to change the stations at which said capillary array units stay, respectively,
   wherein said stations include a sample injection station for injecting fluorophore-labeled samples into each of said capillaries; a fluorescence detection station for irradiating said samples separated by electrophoresis in each of said capillaries with laser beam and detecting fluorescence emitted from the samples; and a medium replacing station for replacing the electrophoresis medium of each of said capillary array units with fresh medium or a sample removing station for removing the residual samples remaining in each of said capillary array units after completion of the separation by electrophoresis, and
   the detection of said fluorescences, the injection of said samples and the removal of said residual samples are repeated at the different stations, respectively, by transferring the plurality of said capillary array units to the different stations, respectively, with said transferring unit.

18. An analyzer according to claim 17, wherein said transferring unit changes the stations at which the plurality of said capillary array units stay respectively, by rotating said capillary array holder.

19. An analyzer according to claim 17, wherein said transferring unit changes the stations at which the plurality of said capillary array units stay, respectively, by the linear motion of said capillary array holder.

20. A fluorescence detection capillary array electrophoresis analyzer comprising:
   a capillary array holder holding first, second and third capillary array units at different stations,
   a transferring unit for transferring said capillary array units in order to change the stations at which said first, second and third capillary array units stay, respectively,
   a sample injecting means for injecting samples labelled with fluorophores into each of capillaries of said first capillary array unit,
   a fluorescence detecting means for detecting fluorescence emitted from said fluorophores labelling samples migrating in said second capillary array unit by irradiating laser beams, and
   a medium replacing means for replacing the electrophoresis medium of said third capillary array unit by fresh one or a sample removing means for removing residual samples remaining in said third capillary array unit.

21. A fluorescence detection capillary array electrophoresis analyzer comprising:

a plurality of capillary array units for separating fluorophore-labeled samples by electrophoresis, and a transferring unit for transferring said capillary array units in turn to a fluorescence detection station at which migrating samples are irradiated with laser beams and fluorescences emitted by said fluorophores are detected.

22. An electrophoresis method using the fluorescence detection capillary array electrophoresis analyzer according to claim 20 which comprises:

a step of holding first, second and third capillary array units at different stations, a step of injecting samples labeled with fluorophores into said first capillary array unit, a step of detecting fluorescence emitted from said fluorophores by irradiation of said samples electrophoresed in said second capillary array unit with laser beams, a step of replacing an electrophoresis medium of said third capillary array unit, or removing residual samples remaining in said third capillary array unit, and a step of transferring said capillary array units in order to change the stations at which said first, second and third capillary array units are held, respectively.

* * * * *